United States Patent [19]

Walsh

[11] Patent Number: 4,795,562

[45] Date of Patent: Jan. 3, 1989

[54] MEMBRANE BATCH-PROCESSING APPARATUS

[76] Inventor: James W. Walsh, 3823 Beech Ave., Baltimore, Md. 21211

[21] Appl. No.: 776,050

[22] Filed: Sep. 13, 1985

[51] Int. Cl.$^4$ .............................................. B01C 13/00
[52] U.S. Cl. ..................................... 210/232; 210/351; 210/456
[58] Field of Search ............... 210/456, 350, 351, 352, 210/651, 232; 436/50, 150

[56] References Cited

U.S. PATENT DOCUMENTS

| | | | |
|---|---|---|---|
| 3,332,216 | 7/1967 | Stern | 55/158 |
| 3,488,690 | 1/1970 | Ross et al. | 210/321 |
| 3,660,280 | 5/1972 | Rogers | 210/22 |
| 3,757,947 | 9/1973 | Wakefield et al. | 210/321.2 X |
| 4,140,637 | 2/1979 | Walder | 210/321 R |
| 4,401,566 | 8/1983 | Igari et al. | 210/351 |

FOREIGN PATENT DOCUMENTS

82/03568 10/1982 PCT Int'l Appl. .

Primary Examiner—Frank Spear
Attorney, Agent, or Firm—Cushman, Darby & Cushman

[57] ABSTRACT

A membrane batch-processor system and method for the fluid treatment of a plurality of specimen containing membranes, such as membranes having specimens of DNA, RNA, and protein molecules deposited thereon, includes a receptacle having an interior cavity and a plug-like closure slidably received in the cavity. A membrane stack is assembled from a plurality of membranes to be treated and flow definers interleaved between the membranes to defined a membrane stack of alternate flow definers and membranes. The flow definers are preferable fabricated from an open-weave fabric-like material to define multiple fluid pathways across the opposite surfaces of each membrane. Fluid distribution plenums are defined between to the receptacle and closure so that treatment fluid introduced into an entry plenum will flow through the multiple fluid pathways across the opposite surfaces of each membrane to expose each membrane to the treatment fluid and effect time and fluid efficient treatment of the membranes.

30 Claims, 5 Drawing Sheets

MEMBRANE BATCH-PROCESSING APPARATUS

CROSS-REFERENCE TO RELATED APPLICATION

The present invention is related to the subject matter disclosed in applicant's co-pending U.S. patent application Ser. No. 694,773, filed Jan. 25, 1985 and entitled, "MEMBRANE PROCESSING SYSTEM AND METHOD," the disclosure of which is incorporated herein by reference.

BACKGROUND OF THE INVENTION

The present invention relates generally to those apparatus and methods of analysis and investigation which utilize a solid support in the form of membranes or similar media upon which selected specimens are transferred to or otherwise placed for analysis and evaluations. More particularly, the present invention relates to and is suited for use in those areas of biotechnology and molecular biology that utilize membranes upon which selected specimens are deposited for analysis, investigation, hybridization, and the like, such specimens including molecules and molecule fragments of DNA, RNA, and proteins.

Many laboratory and analytical procedures involve the use of a sheet-like membranes, such as nitrocellulose, treated nitrocellulose, and similar materials, upon which one or more specimens are deposited with the membrane then subjected to further processing steps to analyze, identify, or isolate selected fragments of the specimens. For example, in the investigation of nucleic acids, the study of the structure and characteristics of DNA and RNA, and the function of selected enzymes in dividing DNA and RNA molecules into fragments of varying size, the use of sheet-like membranes, particularly those of nitrocellulose, are central to isolating selected fragments having certain characteristics. The membranes used are typically quite thin (e.g., 0.001 to 0.005 inch) and formed as rectangles or circular discs, an 82 mm. diameter being the most common for circular disc membranes. Various membrane-utilizing processes have been developed for the investigation of nucleic acids; these processes have in common the step of transferring or otherwise depositing DNA or RNA specimens onto a membrane. The membrane is then subjected to subsequent processing in accordance with the particular methodology of the process. For example, in one process, termed the "dot" blot procedure, fragments of DNA molecules of unlike size are separated, for example, by ultra-centrifuging or column chromatography, into separate samples of like size. The separate samples are then deposited onto a nitrocellulose membrane with each sample occupying a dot-like area on the membrane. In another process, termed the "Southern" blot procedure, fragments of DNA molecules of unlike size are electrophoretically separated into groupings of similar size. The fragments are then transferred to a nitrocellulose membrane for subsequent processing to produce a visible indication, for example, by autoradiograph, of the position on the membrane of the target fragments. Regardless of the particular transfer mechanism employed, the resulting membrane will have groupings of DNA molecule fragments bound thereto.

The membrane is then subjected to a number of fluid treatment steps to identify a particular grouping of target DNA fragments on the membrane. Typically, the transferred DNA fragments are thermally 'fixed' to the membrane by heating at a selected temperature for a period of time sufficient to effect fixing. In order to locate a group of particular target fragments bound to the membrane, a solution of DNA or RNA 'probe' fragments complementary to the target fragments is prepared with the probe fragments coupled to a radioactive tracer material. The membrane is then washed in the probe solution, for example, by immersion in a capped bottle or container or in a heat-sealed plastic bag containing the probe solution, for an incubation period sufficient to allow the radio-tagged probe fragments to hybridized with their complementary target fragments on the membrane. Once sufficient time for annealing has lapsed, the membrane is then washed and treated in a series of buffer solutions, such as ribonuclease, at differing temperatures and concentrations designed to removed the excess unhybridized probe solution. The resulting membrane is dried and retains only the original DNA fragments and the hybridized probe and target radio-tagged fragments. Thereafter, the membrane is processed to yield a visible indication of the location of the annealed target/probe molecules. Typically, the visible indication is obtained by laying the membrane against one side of a radiation sensitive film so that the film is exposed by beta particle radiation from the radioactive tag. The location of the hybridized probe/target molecule fragments on the membrane is revealed by the developed film.

Conventional membrane-dependent procedures are generally labor intensive and require a rather high level of skill to insure valid and reproducible results and minimize physical damage to or contamination of the membrane. Also, the use of membranes is not conducive to time and cost efficiencies that would allow transfer the membrane-based methodologies to clinical, industrial, and agricultural applications where cost and time effectiveness is imperative.

In applicant's cross-referenced patent application, apparatus and method are disclosed for the time and cost efficient treatment of membrane in which the membrane specimen is mounted between leaves of a fabric-like material and inserted into a sealable, flexible walled jacket to create flow passages or channels on opposite sides of the membrane with the probe and buffer solutions introduced and removed through appropriate ports. Numerous flow channels are created across the surfaces of the membrane by the fabric-like leaves to result in the cost and time efficient treatment of the membrane. While the apparatus and method disclosed in applicant's cross-referenced patent application is well suited for its intended purpose, the apparatus can be used to treat one or a small number of membranes at one time. While treatment of one or a small number of membranes meets the needs of many users, a class of users exists which has need to process a large number of membranes simultaneously, such users including research institutions where a large number of membranes must be screened in a time and cost efficient manner. For these users, an apparatus that is limited to treating one or a small number of membranes represents a less than optimum solution to volume screening situations.

SUMMARY OF THE INVENTION

In view of the above, it is an object of the present invention, among others, to provide apparatus and method for the batch or volume processing of solid support membranes and support media used in the analysis and investigation of membrane-supported specimens.

It is also an object of the present invention to improve methodologies for the batch or volume processing of membranes used in molecular biology by decreasing time and costs associated with such processes.

It is another object of the present invention to provide improved apparatus and methodology for the batch or volume processing of membranes used in molecular biology which reduces the opportunity for mishandling and contamination.

It is a further object of the present invention to provide improved apparatus and methodology for the processing of membranes and similar materials used in molecular biology so as to provide a convenient method for the fluid processing of the membranes on a batch or volume basis.

It is still a further object of the present invention to provide improved apparatus and methodology for the processing of membranes that are better suited for clinical, industrial, and agricultural applications and machine-automated processing compared to prior apparatus and methodology.

In accordance with these objects and others, the present invention provides apparatus and methodology for improved procedures involving the use and treatment of solid support membranes having molecular specimens thereon. A membrane processor includes a receptacle having an interior cavity for accepting a membrane stack and a cooperating closure for placement in the open end of the cavity to define a fluid treatment chamber. A membrane stack is assembled from a plurality of membranes to be treated and interleaved flow definers fabricated from a material that creates or defines multiple fluid pathways across the opposite surfaces of the membranes. Fluid ports and distribution plenums are provided so that treatment fluid introduced through an inlet port is distributed by an inlet plenum to flow through the multiple fluid pathways defined on the opposite sides of each membrane to expose all surface areas of the membranes to the treatment fluid in a time and fluid efficient manner.

In the preferred embodiment, a receptacle is provided with a cylindrical cavity for accepting a membrane stack assembled from circular membranes and flow definers. Each flow definer is formed from an open-weave fabric-like material that defines a multitude of fluid pathways across the opposite surfaces of each membrane. A cylindrical plug-like closure is inserted into the open end of the cavity to define a treatment chamber and is slidable relative to the receptacle to contact and contain membrane stacks of different heights. Fluid inlet and outlet ports are provided in the closure for communications with fluid distribution plenums for introducing and removing treatment fluids from the treatment chamber.

In operation, a membrane stack is assembled by alternating or interleaving membranes and flow definers and is placed in the receptacle cavity and maintained in position by the closure. One of the fluid ports is connected to a vacuum source while the other is connected to a source of treatment fluid. The pressure differential causes the closure to advance into the cavity to contact and constrain the membrane stack and also draws treatment fluid into the one port with the fluid distributed by the inlet plenum to flow across the surfaces of each membrane in the multiple fluid pathways created by the flow definers to expose all surface areas of the membrane.

In alternate embodiments, the closure can be formed with a flexible or elastomeric diaphragm that engages and constrains the membrane stack, and the membrane processor can be configured to accept membrane stacks assembled from rectangular membranes, such as those obtained as a result of the "Southern" blot procedure, and rectangular flow definers. In addition, spacers of either a resilient or rigid material may be used to assist in constraining the membrane stack within the membrane processor.

It is contemplated that the best mode of the present invention is an analytical procedures involving the identification of selected molecules bound to a membrane, especially DNA and RNA molecules and molecule fragments and proteins.

The present invention thus provides apparatus and methods for generally improving procedures involving the volume or batch handling and treatment of membranes, particularly procedures involving the analysis of membrane-bound DNA, RNA, and proteins, in such a way that the procedures are more time, material, and cost efficient to provide improved procedures better suited for clinical, industrial, and agricultural applications and eventual automation. The improved procedures consequent to the present invention provide greater immunity to mis-handling and damage of the specimen-bound membrane as well as reduced vulnerability to contamination.

Other objects and further scope of applicability of the present invention will become apparent from the detailed description to follow, taken in conjunction with the accompanying drawings, in which like parts are designated by like reference characters.

DESCRITPION OF THE PREFERRED EMBODIMENT

Figure 1:
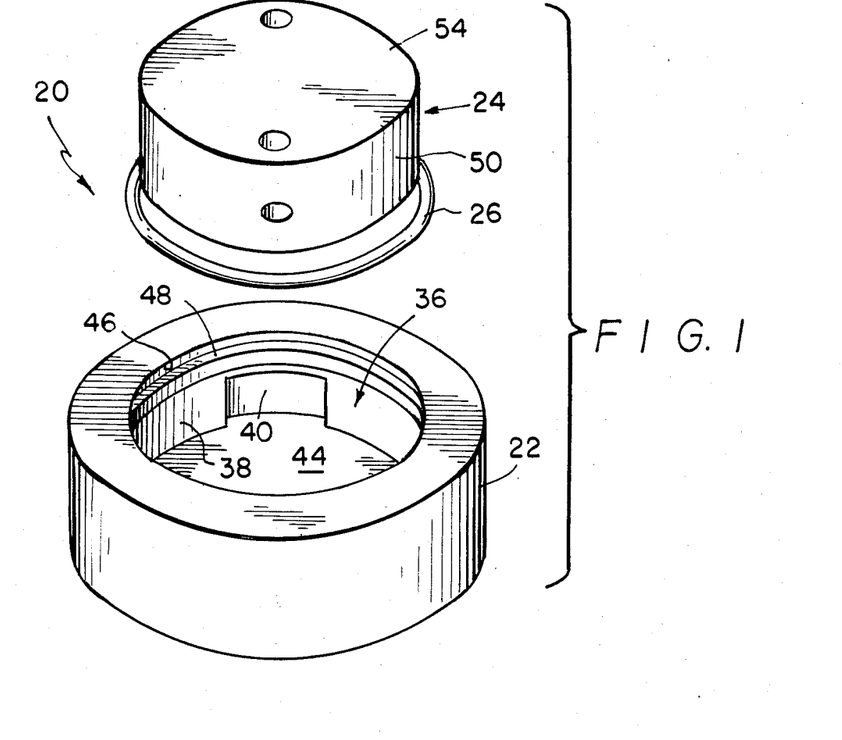
FIG. 1 is an exploded isometric view of a preferred embodiment of a membrane batch-processing system in accordance with the present invention.

A preferred embodiment of a membrane processor in accordance with the present invention is illustrated in FIG. 1 and designated generally by the reference character 20. As shown, the membrane processor 20 includes a base-like receptacle 22, a plug-like closure 24, and a seal 26. In the preferred embodiment, the membrane processor 20 is designed to accommodate 82 mm. circular membranes and can be reconfigured to accommodate membranes of different diameters or shapes.

Figure 2:
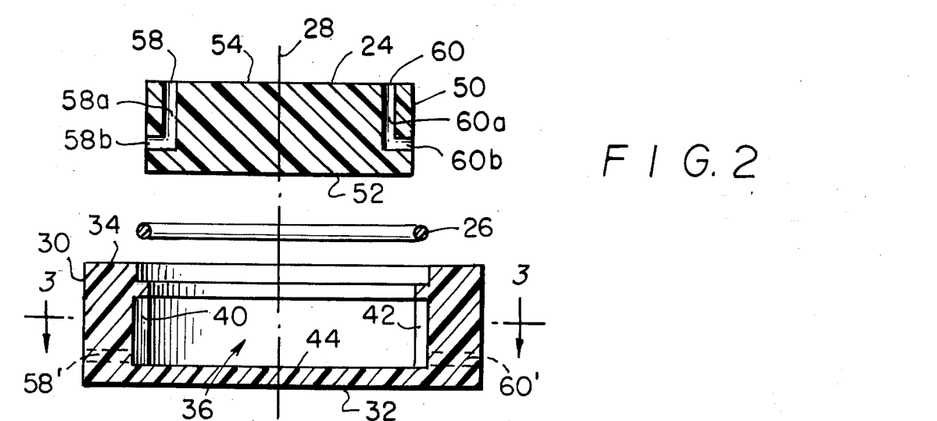
FIG. 2 is a side elevational view, in cross section, of an assembled membrane batch-processing system.
Figure 3:
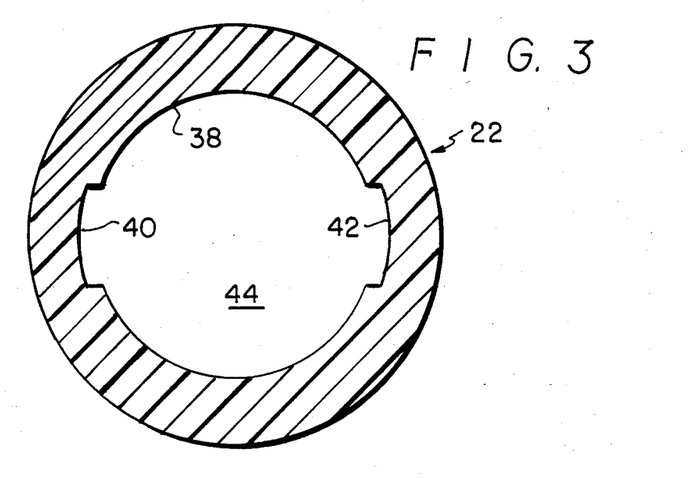
FIG. 3 is a plan view, in cross section, of the membrane batch-processing system of FIG. 2 taken along line 3—3 of FIG. 2.

As shown in FIGS. 2 and 3, the receptacle 22 is formed as a cylindrical body of revolution about an axis 28 and includes a cylindrical sidewall 30, a bottom surface 32, and top or upper surface 34. The receptacle 22 is formed with a cavity, generally indicated as 36, which is defined by a cylindrical interior surface 38 that is interrupted by radially enlarged areas which, as described below, define fluid distribution plenums 40 and 42, and an interior bottom surface 44. Additionally, a counterbore defined by a cylindrical surface 46 and an annular surface 48 is formed at the mouth or open end of the cavity 36. In the preferred embodiment, the interior surface 38 is formed at a diameter sufficient to provide a clearance fit for accepting 82 mm. membranes as described more fully below.

The closure 24 is formed as a cylindrical body of revolution and includes a cylindrical sidewall 50, a bottom surface 52, and a top or upper surface 54. The closure 24 is formed with a diameter dimension that is somewhat less in the inside diameter dimension of the interior cylindrical wall 38 to define a clearance or slip fit between the two components. Fluid ports 58 and 60 are formed in the closure 24 on opposite sides for introducing and removing fluids from the assembled membrane processor 20. The fluid ports 58 and 60 are defined, respectively, by axially aligned portions 58a and 60a and radially aligned portions 58b and 60b. Other port configurations are suitable, including, as shown in dotted line illustration in FIG. 2, ports 58' and 60' formed through the cylindrical sidewall of the receptacle 22 and opening into and communicating with the plenum areas 40 and 42.

The seal 26 is a conventional O-ring for placement in the counter bore defined by the surfaces 46 and 48 for engaging the cylindrical wall 50 of the closure 24. While the seal 26 can be captured in a retaining groove rather than placed in the counterbore, the latter arrangement is preferred to facilitate device cleaning and operation. The seal 26 is dimensioned to engage the sidewall 50 of the closure 24 with a sliding fit to allow the closure 24 to extend into the cavity 36 while maintaining a fluid-tight seal.

The receptacle 22 and the closure 24 are preferably fabricated from a molded or machined plexiglass although other materials that are inert to the processed materials and the processing fluids are suitable.

Figures 4, 4A:
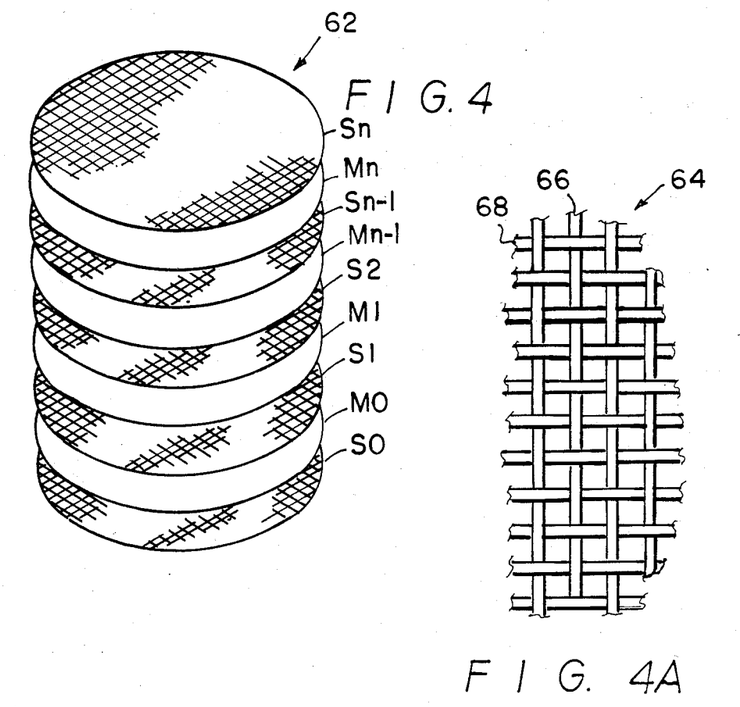
FIG. 4 is an expanded isometric view of a membrane stack assembled from a plurality of membranes and interleaved flow definers.
FIG. 4a is a detail plan view of a portion of a flow definer.

The membrane processor 20 is designed to process a membrane stack 62, shown in exploded view in FIG. 4, which is assembled from membranes $M_0, M_1, \ldots M_{n-1}, M_n$ and interleaved or alternating flow definers $S_0, S_1, \ldots S_{n-1}, S_n$. The membrane stack 62 is assembled in such a way that each membrane $M_n$ has a flow definer $S_n$ on opposite side surfaces. The membranes $M_n$, as described above, are typically 0.001 to 0.005 inch thick nitrocellulose or treated nitrocellulose upon which DNA, RNA, or other molecular fragments have been placed. In the preferred embodiment, the membranes $M_n$ have a standard 82 mm. diameter. The flow definers $S_n$ are preferably formed from circular discs of an open weave sheet-like polyethylene fabric 64 with a diameter generally equal to that of the membranes $M_n$, although the flow definer $S_n$ diameter can be larger or less than that of the membrane $M_n$. As shown in FIG. 4a, the fabric 64 has orthogonal weft threads 66 and woof threads 68 that create numerous interstitial areas and cavities therebetween. Treatment fluid in any one interstitial area can flow to adjacent interstitial areas and thus flow across the surfaces of the membrane $M_n$ in the multiple fluid pathways created by the flow definer. In the preferred embodiment, a fabric thickness of five to ten mils woven from a 75 to 95 micron fiber with a thread count of between 40 and 120 per inch for the weft and woof threads has been found satisfactory. While an open-weave fabric is preferred, other materials including non-woven polypropylene spun-bonded materials and sheets or webs having textured, undulating, perforated, or corrugated surface characteristics that cooperate with the membranes to form multiple fluid pathways across the surfaces of the membranes have been found satisfactory. The rotary alignment of the orthogonal threads of the flow definers $S_n$ relative to the plenums 40 and 42 does not appear to affect fluid treatment efficiency.

Figure 5:
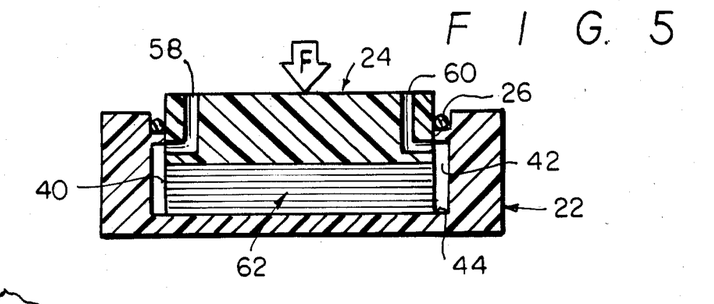
FIG. 5 is a side elevational view, taken along a diameter, of the assembled membrane batch-processor and the membranes and interleaved flow definers of FIG. 4.

After a membrane stack 62 is assembled, it is processed by placement in the cavity 36, as shown in FIG. 5, with the lower most flow definer resting upon the bottom surface 44 of the cavity 36 and with the peripheral edges of the membranes $M_n$ and the flow definers $S_n$ contained by the interior wall 38. The closure 24 is fitted into the open end of the cavity 36 with the seal 26 maintaining engagement with the cylindrical wall 50 of the closure 24. The closure 24 is aligned with the receptacle 22 so that the ports 58 and 60 communicate, respectively, with the plenums 40 and 42. Where the fluid ports are provided in the receptacle 22, as in the case of the ports 58' and 60' of FIG. 2, no particular alignment of the closure 24 is necessary. The closure 24 is manually advanced into the cavity 36 until the bottom surface 52 of the closure 24 contacts the top of the membrane stack 62 so that the receptacle 22 and the closure 24 define a closed treatment chamber. Since the closure 24 can be moved manually in the cavity 36, membrane stacks 62 of varying height can be accommodated. While the membrane processor 20 is intended to allow treatment of membranes on a volume or batch basis, such as 50-70 membranes at a time, the membrane processor 20 can accommodate and treat membrane stacks with as few as one membrane and two flow definers.

Figure 6:
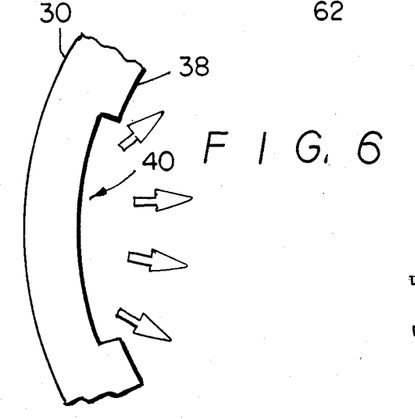
FIG. 6 is a detail view, in cross section, illustrating the flow distribution pattern from a fluid inlet plenum.

The axial portions 58a and 60a of the fluid ports 58 and 60 are formed with a converging taper and are sized to accept a force fit engagment with a "Luer" type fitting to allow convenient connection to supply and discharge tubing (not shown in FIG. 5). As shown in FIGS. 5 and 6, the plenums 40 and 42 extend along the full height of the membrane stack 62 with the plenums extending peripherally over a portion of the circumference of the membrane stack 62, a peripheral extension of between 10° and 40° being satisfactory in the case of the preferred embodiment.

In operation, a treatment fluid is introduced into one of the ports, for example, the port 58, to fill the respective plenum 40 while the other port 60 is connected to a vacuum source. The vacuum source lowers the internal pressure in the cavity 36 relative to the ambient pressure and causes the closure 24 to advance against the top of the membrane stack 62 and slightly compress the membrane stack 62 as a function of the pressure differential. Since the closure 24 is movable, it will readily self-adjust to the height of the membrane stack 62. In general, the pressure differential between the cavity 36 and ambient pressure should be sufficient to maintain the closure 24 in contact with the membrane stack 62 but not so great as to cause undue compression. While the compressive force generally assists in causing the flow defines $S_n$ to uniformly contact the opposite sides of each membrane $M_n$, such uniform contact is not essential to efficient operation. Thus, the compressive force can be such that only portions of the surface area of the flow definers $S_n$ contact the opposite sides of the membranes $M_n$ while other portions of the surface are do not contact and are adjacent to the membrane $M_n$. If desired, a mechanical force F may be applied to the closure 24 to maintain contact with the membrane stack 62, the force being applied, for example, by an adjustable clamp, by a weight, or a suitably fixtured biasing spring or element (not shown).

Figure 7:
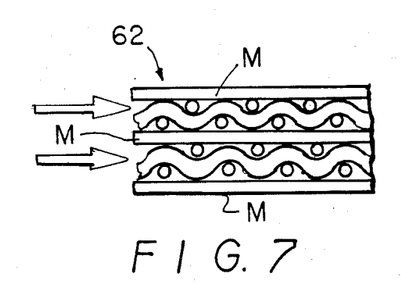
FIG. 7 is a side view, in cross section, of several interleaved membranes and flow definers illustrating the manner in which treatment fluid flows across the membrane.

As shown in the detail view of FIG. 7, each membrane $M_n$ is constrained between flow definers $S_n$ with the undulations of the woven flow definer $S_n$ on the opposite sides of the membrane $M_n$ creating or defining a multitude of fluid flow pathways across the opposite surfaces of the membrane $M_n$. Fluid introduced into the port 58 and the plenum 40 will be distributed along the full height of the membrane stack 62 and across the periphery subtended by the plenum 40. Because of the pressure differential between the inlet port 58 and the outlet port 60, the fluid introduced into the plenum 40 will flow across the opposite surfaces of each membrane $M_n$ to thoroughly expose and treat the membrane $M_n$ to the fluid. In dimensioning the inside diameter of the cylindrical surface 38 relative to the outside diameter of the membranes $M_n$, it is desirable to allow a clearance space to facilitate insertion and removal of the membrane stack 62, although the clearance should not be so large as to create peripheral passageways which serve as bypasses between the inlet plenum 40 and the outlet plenum 42. The creation of such bypass passageways can increase the treatment time required as well as increase the quantity of fluid required for treatment.

Figure 8:
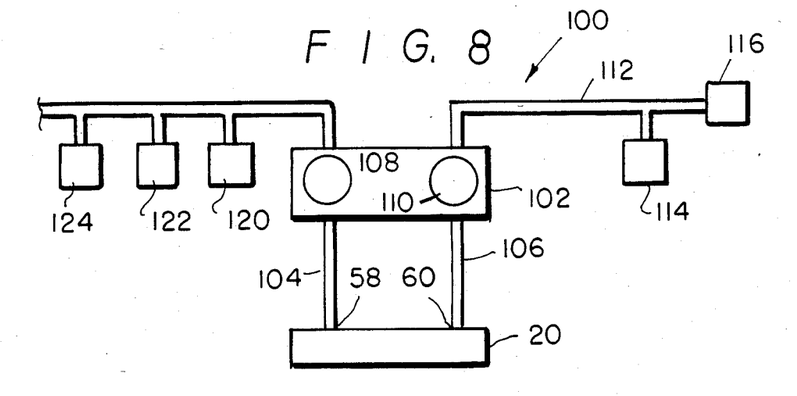
FIG. 8 is a schematic illustration of a system for introducing and removing treatment fluids from the membrane batch-processor.

A system for the treatment of membranes $M_n$ is shown in schematic form in FIG. 8 and designated generally therein by the reference character 100. As shown, the system 100 includes a valve unit 102 connected to the membrane processor 20 by a connecting tube 104 coupled to the port 58 and another connecting tube 106 coupled to the port 60. The valve unit 102 includes a manual valving control 108 and a manual valving control 110 for controlling the rate of and interrupting the fluid flow to the ports 58 and 60. The manual valving control 110 is coupled through a connecting tube 112 to a fluid trap 114 and a vacuum source 116 while the manual valving control 108 is coupled through a connecting tube 118 to a plurality of fluid sources, including fluid source 120, fluid source 122, and fluid source 124, with the various fluid sources containing fluids necessary to the treatment of the membranes in the membrane stack 62. Each fluid source includes valving (not shown) for selectively introducing the respective fluid into the connecting tube 118.

In order to process a membrane stack 62, a probe solution containing radio-tagged DNA and RNA molecules complementary to the target molecules is introduced into the membrane processor 20 through one of the ports 58 or 60 with any trapped or excess air aspirated from the cavity by the vacuum source 116. In order to effect hybridization of the probe and the target fragments, the temperature of the fluids must be maintained at a desired hybridization temperature (about 65° C.) for a period of time sufficient to effect annealing of the probe and target fragments. The desired temperature can be attained, for example, by placement of the membrane processor 20 in a heated water bath, preheating the fluids prior to their introduction into the membrane processor 20, or by a combination of the heated water bath and preheating the fluids.

As an alternative to the introduction of the fluids using the system of FIG. 8, the probe solution and the aspiration of the trapped or excess air may be effected manually by hypodermic syringe. The ports 58 and 60 can then be sealed with appropriate stoppers (not shown), and the sealed membrane processor 20 placed in an oven or water bath for an incubation period sufficient to effect annealing of the probe and target fragments.

After annealing is completed, the bulk of the probe solutions is removed from the membrane processor 20 by the vacuum source 116. The membrane stack 62 is then washed by controlling the manual valving controls 108 and 110 to reduce the pressure in the interior of the membrane processor 20 while allowing a wash solution to be introduced into the port 58 from one or more of the fluid sources 120, 122, or 124. As mentioned above, the application of the vacuum causes the closure 24 to self-adjust to accommodate the height of the membrane stack 62 and to slightly compress the membrane stack 62. After a first wash solution is passed through the cavity 36, a second and third wash solution may be passed through the cavity 36 to achieve complete washing of the membrane stack 62.

During application of the treatment fluids, the fluid flows in an expanding pattern or front from the inlet plenum across the surfaces of the membranes toward and to the outlet plenum. While the pressure differential existing between the fluid ports 58 and 60 motivates the flow of the various fluids, it is also believed that the multiple fluid pathways assist by functioning as capillaries. The washing results in the removal of unhybridized probe solution leaving the membranes $M_n$ with their original fragments and the annealed radio-tagged probe and target fragments. The multiple fluid pathways defined across the surfaces of the membranes are believed to expose all portions of the membranes to the fluid flow in such a way that the fluid treatment is efficiently accomplished in a time and fluid efficient manner without exposing the membranes $M_n$ to any potentially damaging fluid flow conditions.

If desired, air can be entrained in the wash fluid by introducing or otherwise aspirating air into the connecting tube 118. It has been found that a moderate amount of entrained air does not reduce the effectiveness of the washing and results in the use of substantially less wash fluid.

The various fluid treatment steps can be conducted in a serial manner, with or without the use of entrained air, and, if desired, with one or more intermediate "air" washings. In this latter case, air is allowed to enter the inlet port 58 to cause the liquid from the prior fluid treatment to be entirely discharged from the cavity 36 prior to the introducing of the next fluid in the treatment sequence. Air washings aid in the removal of any residual liquids by entraining droplets in the air flow and transporting the droplets to the exit port 60.

Figures 9, 10:
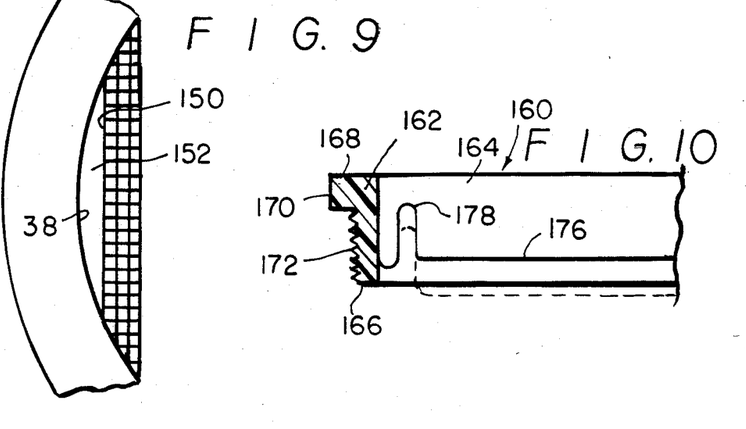
FIG. 9 is a detail view illustrating an alternate structure for creating a distribution plenum.
FIG. 10 illustrates an alternate embodiment of a closure for the membrane batch-processor.

In the preferred embodiment, discrete plenums are defined by radially enlarged portions of the interior wall 38 that defines the cavity 36. While plenums are preferred, other distribution arrangements that accomplish an equivalent fluid distribution function are suitable. For example and as shown in FIG. 9, the membranes $M_n$ and the flow definers $S_n$ can each be formed with portions along a chordal line 150 removed to define a plenum-equivalent 152 with the interior wall 38. The fluid ports 58 and 60 are modified to be axial portions only so that fluid communications will be with the plenum 152.

The closure 24 has been illustrated as a rigid structure that is slidable relative the receptacle 22 to allow the closure 24 to accommodate to the membrane stack 62 height. As shown in FIG. 10, an alternate form of the closure, designated generally by the reference character 160, includes an annular body 162 defined by a cylindrical interior wall 164, a bottom wall 166, and a top or upper wall 168. The exterior wall is defined by a flange-like rim 170 and a reduced diameter threaded portion 172. An interior wall portion of the receptacle (not shown in FIG. 10) is threaded in a complementary manner to accept the closure 160. A diaphragm, generally designated by the reference character 174, is secured to the interior wall 164 of the closure 160 and includes a central discoidal portion 176 and at least one peripheral convolution 178. The diaphragm 174 can be fabricated from a material that is inert to the processing fluids and the processed materials, for example, a polyethylene or elastomeric sheet material that is secured along its periphery by adhesive or other bonding techniques to the interior wall 164. The convolution 178 or convolutions is preferably pre-formed in the diaphragm 174 by thermal setting while the material is suitable restrained. If desired, the discoidal portion 176 can be augmented with a rigid disc (not shown).

The closure 160 is mated to its receptacle (not shown) by threading the two components together with the rim 170 engaging the seal. When the membrane processor 20 is connected to a vacuum source, as described above, the diaphragm 174 will advance into the cavity 36 to engage the top of the membrane stack 62 in the manner described above.

Figure 11:
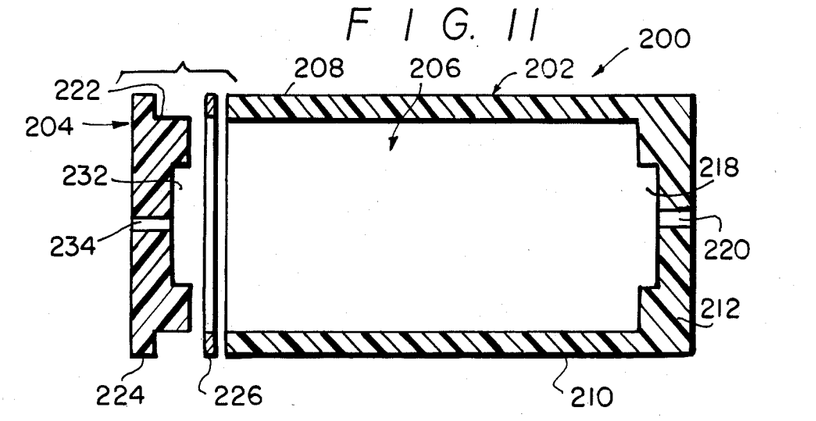
FIG. 11 is a top view, in cross section, of an alternate form of the membrane batch-processor for treating rectangular membranes.

The preferred embodiment of the membrane processor described above is designed to accommodate circular membranes. An embodiment for rectangular membranes is illustrated in FIG. 11 and designated generally by the reference character 200. As shown, the membrane processor 200 includes a receptacle 202 and a closure 204. The receptacle 202 is formed as an open-ended paralellipiped with an interior cavity 206 defined by sidewalls 208 and 210, an end wall 212, and a bottom wall 214 and a top wall (not shown). The end wall 212 is formed with a fluid distribution plenum 218 and a fluid port 220. The closure 204 includes a block-like extension 222 for insertion into the interior cavity 206 and a rim 224 for capturing a seal or gasket 226 against the opposing end surface 230 of the receptacle 202. A fluid distribution plenum 232 and fluid port 234 are formed in the closure 202. Since the receptacle 202 is formed as a rigid walled structure, the membrane stack (not shown) assembled from rectangular membranes and similarly shaped flow definers must be within selected height dimensions to be properly accommodated within the receptacle 202.

In operation, the rectangular membrane stack (not shown) is inserted end-wise into the receptacle 202 and the closure 204 inserted into the open end to close the interior cavity 206 with the gasket 226 mounted between the two. One of the fluid ports, for example, the fluid port 220 is connected to a vacuum source while the other fluid port 234 is connected to a source of treatment fluid. The pressure differential between the interior cavity 206 and ambient assists in maintaining the closure 204 in position and draws fluid from the fluid source through the port 234 and into the plenum 232. The fluid flows across the surfaces of the membranes in the multiple fluid pathways created by the flow definers to expose each of the membranes to the fluid with the fluid accumulating in the plenum 218 for discharge through the fluid port 220.

Figure 12:
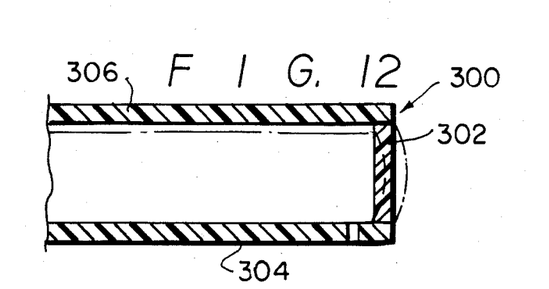
FIG. 12 is a partial side view, in cross section, of a alternate flexible sidewall structure for a membrane processor.

A further embodiment of a membrane processor is illustrated in FIG. 12 and designated therein generally by the reference character 300. In contrast to the membrane processor 200 of FIG. 11, the membrane processor 300 is constructed with elastomeric sidewalls 302 to permit dimensional changes to accommodate membrane stocks of different stack height. The membrane processor 300 includes a lower rigid wall 304 and an upper rigid wall 306 with one of the walls secured to the resilient sidewall 302 and the other removeable. The elastomeric sidewalls 302 may be formed form pre-molded silicone and can include corrugations or pleats to provide a measure of flexure.

Figure 13:
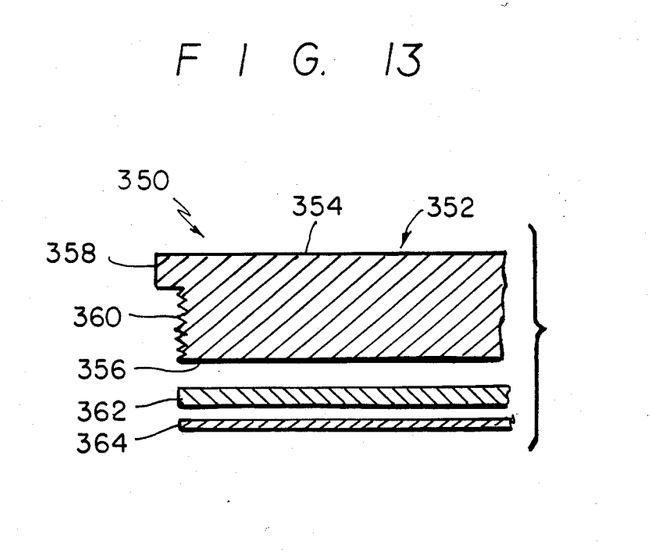
FIG. 13 is another alternate embodiment of a closure for the membrane batch-processor.

A further embodiment of a closure system for a membrane processor is illustrated in FIG. 13 and is designated generally therein by the reference character 350. As shown the closure system includes a closure 352 defined as a circular body fabricated from a rigid material having a top surface 354, a bottom surface 356, a flange-like radially extending rim 358, and a reduced diameter threaded portion 360 for engaging a complementary threaded portion of the receptable (not shown). In order to accommodate membrane stacks 62 of different heights, a supply of spacers or shims of varying thickness, as represented by the shims 362 and 364 of FIG. 13, are provided. Shims having the proper thickness dimensions are assembled to take up any clearance space between the top of the membrane stack 62 and the bottom surface 356 of the closure 350 to thus constrain and accommodate membrane stacks 62 of varying height. The shims may be fabricated from a rigid material or, if desired, from a resiliently compressible material, preferably having a fluid impervious skin to avoid absorption or contamination of any of the treatment fluids.

Thus it will be appreciated from the above that as a result of the present invention, a highly effective membrane batch-processing system and method is provided by which the principal objective, among others, is completely fulfilled. It will be equally apparent and is contemplated that modification and/or changes may be made in the illustrated embodiment without departure from the invention. Accordingly, it is expressly intended that the foregoing description and accompanying drawings are illustrative of preferred embodiments only, not limiting, and that the true spirit and scope of the present invention will be determined by reference to the appended claims.

What is claimed is:

1. An apparatus for subjecting molecules and molecule fragments supported upon sheet-like membranes to a fluid treatment, said apparatus comprising:
    a container including at least first and second components cooperating with one another to define a fluid treatment cavity, the components having first and second substantially parallel, opposed planar surfaces defining the cavity, at least one surface thereof moveable toward and away from the other to vary the size of the cavity;
    at least first and second flow definers having a membrane to be treated therebetween and positioned within the cavity, said membrane having molecular specimens placed thereon, said flow definers defining multiple fluid pathways across the opposite surfaces of the membrane, said flow definers and said opposed planar surfaces of said first and second components having surface areas at least coextensive with that of the membrane to be treated;
    inlet port means for introducing a fluid into the cavity along a portion of the periphery of said first and second flow definers and the membrane to be treated; and
    outlet port means for removing a fluid from the cavity along another portion of the periphery of said first and second flow definers and the membranes to be treated;
    said multiple fluid pathways conducting treatment fluid uniformly in the same direction across the opposite surfaces of the membrane from said inlet port means to said outlet port means, wherein;
    said molecular specimens are treated by said treatment fluid.

2. The apparatus of claim 1 wherein said one component comprises a receptacle having a cavity formed therein and said other component comprises a closure for engagement with said receptacle to define said fluid treatment cavity.

3. The apparatus of claim 2, wherein said closure is moveable relative to a surface of the cavity to varying the volume of the cavity.

4. The apparatus of claim 2, wherein said receptacle has a cavity defined by a cylindrical wall surface for accepting circular membranes and flow definers and said closure is formed as a cylinder for insertion into the open end of the cavity.

5. The apparatus of claim 2, wherein said receptacle has a cavity formed therein for accepting rectangular membranes and said closure is effective to close an open end of the cavity.

6. The apparatus of claim 1, further comprising:
    a first fluid distribution plenum associated with said inlet port and a second fluid distribution plenum associated with said outlet port.

7. The apparatus of claim 6, wherein said flow definers and membrane are circular in planview, said first and second flow distribution plenums positioned to introduce and remove treatment fluid on diametrically opposite sides thereof.

8. The apparatus of claim 1, wherein said flow definers comprise:
    at least one sheet of a material having surface characteristics that define multiple fluid pathways across the surface of a membrane.

9. The apparatus of claim 1, wherein said flow definers comprise:
    at least one sheet of a perforate material having surface characteristics that define multiple fluid pathways across the surface of a membrane.

10. The apparatus of claim 1, wherein said flow definers comprise:
    at least one sheet of a woven material having surface characteristics that define multiple fluid pathways across the surface of a membrane.

11. An apparatus for subjecting molecules and molecule fragments supported upon sheet-like membranes to a fluid treatment, said apparatus comprising:
    a container including at least first and second components cooperating with one another to define a fluid treatment cavity, the components having first and second substantially parallel, opposed planar surfaces defining the cavity, at least one surface thereof moveable toward and away from the other to vary the size of the cavity;
    a membrane stack for placement in the cavity, said membrane stack assembled from interleaved flow definers and membranes to be treated, said membrane having molecular specimens placed thereon, said flow definers defining multiple fluid pathways across the opposite surfaces of the interleaved membranes, said flow definers and said opposed planar surfaces of said first and second components having surface areas at least coextensive with that of the membranes to be treated;
    inlet port means for introducing a fluid into the cavity along a portion of the periphery of said membrane stack; and
    outlet port means for removing a fluid from the cavity along another portion of the periphery of said membrane stack;
    said multiple fluid pathways conducting treatment fluid uniformly in the same direction across the opposite surfaces of the membranes from said inlet port means to said outlet port means, wherein;
    said molecular specimens are treated by said treatment fluid.

12. The apparatus of claim 11, wherein said flow definers comprise:
    at least one sheet of a material having surface characteristics that define multiple fluid pathways across the surface of a membrane.

13. The apparatus of claim 11, wherein said flow definers comprise:
    at least one sheet of a perforate material having surface characteristics that define multiple fluid pathways across the surface of a membrane.

14. The apparatus of claim 11, wherein said flow definers comprise:
    at least one sheet of a woven material having surface characteristics that define multiple fluid pathways across the surface of a membrane.

15. The apparatus of claim 11, further comprising:
    at least one shim for insertion into the cavity between said closure and the membrane stack.

16. An apparatus for subjecting molecules and molecule fragments supported upon sheet-like membranes to a fluid treatment, said apparatus comprising:
    a receptacle having a chamber formed therein;

a closure for insertion into the chamber to define a closed fluid treatment cavity;

the receptacle and closure having first and second substantially parallel, opposed planar surfaces defining endwalls of the cavity, at least one surface thereof moveable toward and away from the other to vary the size of the cavity;

a membrane stack for placement in the cavity, said membrane stack assembled from interleaved flow definers and membranes to be treated, said membrane having molecular specimens placed thereon, said flow definers defining multiple fluid pathways across the opposite surfaces of the interleaved membranes, said flow definers and said opposed planar surfaces of said first and second components having surface areas at least coextensive with that of the membranes to be treated;

inlet port means for introducing a fluid into the cavity along a portion of the periphery of said membrane stack; and outlet port means for removing a fluid from the cavity along another portion of the periphery of said membrane stack;

said multiple fluid pathways conducting treatment fluid uniformly in the same direction across the opposite surfaces of the membranes from said inlet port means to said outlet port means, wherein;

said molecular specimens are treated by said treatment fluid.

17. The apparatus of claim 16, wherein the receptacle is defined by an interior cylindrical wall and an end wall, said closure insertable into the cavity and having a surface that defines a second end wall.

18. The apparatus of claim 17, wherein said closure is adjustably received in the cavity to vary the distance between said first and second end walls.

19. The apparatus of claim 18, wherein said closure is slidably received in the cavity to vary the distance between said first and second end walls.

20. The apparatus of claim 18, wherein said closure is threadedly engageable with said receptacle to vary the distance between first and second end walls.

21. The apparatus of claim 17, wherein one of said first and second endwalls is a rigid surface.

22. The apparatus of claim 17, wherein both of said first and second endwalls is a rigid surface.

23. The apparatus of claim 17, wherein said port means further comprises:
first and second plenums for introducing and removing fluid from the cavity.

24. The apparatus of claim 23, wherein said plenums are formed in said interior cylindrical wall.

25. The apparatus of claim 16, wherein said flow definers comprise:
at least one sheet of a material having surface characteristics that define multiple fluid pathways across the surface of a membrane.

26. The apparatus of claim 16, wherein said flow definers comprise:
at least one sheet of a perforate material having surface characteristics that define multiple fluid pathways across the surface of a membrane.

27. The apparatus of claim 16, wherein said flow definers comprise:
at least one sheet of a woven material having surface characteristics that define multiple fluid pathways across the surface of a membrane.

28. The apparatus of claim 16, further comprising:
at least one shim for insertion into the cavity to vary the volume thereof.

29. The apparatus of claim 28, wherein said shim if formed from a rigid material.

30. The apparatus of claim 28 wherein said shim is formed from a resilient compressible material.

* * * * *